(12) United States Patent
Harris et al.

(10) Patent No.: US 9,987,063 B2
(45) Date of Patent: Jun. 5, 2018

(54) PLATES WITH COUNTERSINKS

(71) Applicant: Stryker European Holdings I, LLC, Kalamazoo, MI (US)

(72) Inventors: Stephen Vaughan Harris, Mesa, AZ (US); Julia Zelenkova, Freiburg (DE); Ediuska V. Laurens, Jersey City, NJ (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 401 days.

(21) Appl. No.: 14/693,109

(22) Filed: Apr. 22, 2015

(65) Prior Publication Data

US 2015/0297273 A1 Oct. 22, 2015

Related U.S. Application Data

(60) Provisional application No. 61/982,640, filed on Apr. 22, 2014.

(51) Int. Cl.
*A61B 17/80* (2006.01)
*A61B 17/00* (2006.01)

(52) U.S. Cl.
CPC .......... *A61B 17/8085* (2013.01); *A61B 17/80* (2013.01); *A61B 2017/00004* (2013.01)

(58) Field of Classification Search
CPC ................. A61B 17/80–17/809; F16B 35/065
USPC ................ 606/70, 71, 280–299; 411/399
See application file for complete search history.

(56) References Cited

U.S. PATENT DOCUMENTS

| | | | | |
|---|---|---|---|---|
| 4,219,015 A | * | 8/1980 | Steinemann | A61B 17/80 606/280 |
| 4,408,601 A | * | 10/1983 | Wenk | A61B 17/8014 606/282 |
| 4,429,690 A | * | 2/1984 | Angelino-Pievani | A61B 17/80 606/280 |
| 4,524,765 A | * | 6/1985 | de Zbikowski | A61B 17/80 606/280 |

(Continued)

FOREIGN PATENT DOCUMENTS

| CN | 202069675 U | 12/2011 |
|---|---|---|
| DE | 8610858 U1 | 6/1986 |

(Continued)

OTHER PUBLICATIONS

Extended European Search Report for Appln. No. EP 15001194 dated Nov. 25, 2015.

*Primary Examiner* — Eric S Gibson
(74) *Attorney, Agent, or Firm* — Lerner, David, Littenberg, Krumholz & Mentlik, LLP

(57) ABSTRACT

A resorbable bone plate includes an elongated base member with a plurality of countersinks formed on the top surface. The countersinks provide a location for screw holes to be drilled through the plate and into a bone. Screws can then be inserted through the holes and into the bone. The countersinks allow the screw heads to remain flush or close to flush to the top surface of the bone plate, thereby reducing the overall profile of the system. The bottom surface of the bone plate is solid to provide significant resistance to deformation. The bone plate can have countersinks formed in a variety of configurations to provide a multitude of options for a surgeon to select a screw insertion location.

21 Claims, 6 Drawing Sheets

(56) References Cited

U.S. PATENT DOCUMENTS

| | | | | |
|---|---|---|---|---|
| 4,794,918 | A * | 1/1989 | Wolter | A61B 17/8042 606/287 |
| 4,905,680 | A * | 3/1990 | Tunc | A61B 17/80 606/280 |
| 5,057,111 | A | 10/1991 | Park | |
| 5,304,180 | A * | 4/1994 | Slocum | A61B 17/8014 606/282 |
| 5,397,363 | A | 3/1995 | Gelbard | |
| 5,709,686 | A * | 1/1998 | Talos | A61B 17/8014 606/280 |
| 5,868,746 | A | 2/1999 | Sarver et al. | |
| 6,139,550 | A * | 10/2000 | Michelson | A61B 17/1604 606/287 |
| 6,221,075 | B1 | 4/2001 | Tormala et al. | |
| 6,692,498 | B1 * | 2/2004 | Niiranen | A61B 17/80 606/70 |
| 6,730,091 | B1 * | 5/2004 | Pfefferle | A61B 17/8057 606/291 |
| 7,740,648 | B2 * | 6/2010 | Young | A61B 17/8014 606/286 |
| 7,935,126 | B2 | 5/2011 | Orbay et al. | |
| 8,172,886 | B2 | 5/2012 | Castaneda et al. | |
| 8,366,751 | B2 | 2/2013 | Pfefferle et al. | |
| 8,834,537 | B2 | 9/2014 | Castaneda et al. | |
| 2001/0047172 | A1 * | 11/2001 | Foley | A61B 17/1728 606/86 B |
| 2002/0120273 | A1 * | 8/2002 | Needham | A61B 17/1728 606/281 |
| 2003/0040749 | A1 * | 2/2003 | Grabowski | A61B 17/7059 606/71 |
| 2004/0039387 | A1 * | 2/2004 | Gause | A61B 17/1728 606/86 B |
| 2005/0015089 | A1 * | 1/2005 | Young | A61B 17/8014 606/915 |
| 2005/0182408 | A1 * | 8/2005 | Pfefferle | A61B 17/8085 606/282 |
| 2005/0283152 | A1 * | 12/2005 | Lindemann | A61B 17/7059 606/281 |
| 2006/0195085 | A1 * | 8/2006 | Happonen | A61B 17/8057 606/281 |
| 2006/0276793 | A1 * | 12/2006 | Berry | A61B 17/8052 606/70 |
| 2007/0055251 | A1 * | 3/2007 | Huebner | A61B 17/8047 606/279 |
| 2007/0055253 | A1 * | 3/2007 | Orbay | A61B 17/80 606/71 |
| 2007/0162011 | A1 * | 7/2007 | Leyden | A61B 17/1721 606/65 |
| 2007/0270852 | A1 * | 11/2007 | Tormala | A61B 17/80 606/281 |
| 2008/0015593 | A1 * | 1/2008 | Pfefferle | A61B 17/8052 606/282 |
| 2008/0039851 | A1 * | 2/2008 | Schulz | A61B 17/15 606/87 |
| 2008/0208259 | A1 * | 8/2008 | Gilbert | A61B 17/8057 606/280 |
| 2009/0254126 | A1 * | 10/2009 | Orbay | A61B 17/151 606/282 |
| 2010/0036430 | A1 * | 2/2010 | Hartdegen | A61B 17/1728 606/281 |
| 2010/0131012 | A1 * | 5/2010 | Ralph | A61B 17/80 606/280 |
| 2010/0131013 | A1 * | 5/2010 | Ralph | A61B 17/80 606/286 |
| 2010/0168799 | A1 * | 7/2010 | Schumer | A61B 17/151 606/286 |
| 2010/0249850 | A1 * | 9/2010 | Cerynik | A61B 17/86 606/281 |
| 2010/0274293 | A1 * | 10/2010 | Terrill | A61B 17/8057 606/286 |
| 2011/0137314 | A1 * | 6/2011 | Kuster | A61B 17/74 606/70 |
| 2011/0184413 | A1 * | 7/2011 | Slater | A61B 17/8061 606/70 |
| 2011/0313421 | A1 * | 12/2011 | Sidebotham | A61B 17/8057 606/70 |
| 2012/0010617 | A1 * | 1/2012 | Ramos Maza | A61B 17/1746 606/70 |
| 2012/0123539 | A1 * | 5/2012 | Hightower | A61B 17/8028 623/11.11 |
| 2012/0203227 | A1 * | 8/2012 | Martin | A61B 17/8061 606/70 |
| 2013/0018424 | A1 * | 1/2013 | Subik | A61B 17/1728 606/281 |
| 2013/0090656 | A1 * | 4/2013 | Huebner | A61B 17/1728 606/70 |
| 2013/0172942 | A1 * | 7/2013 | Lewis | A61B 17/8061 606/281 |
| 2013/0204304 | A1 | 8/2013 | Bottlang et al. | |
| 2014/0039563 | A1 * | 2/2014 | Mocanu | A61B 17/8057 606/291 |
| 2015/0032167 | A1 * | 1/2015 | Heino | B29B 11/08 606/284 |
| 2015/0039033 | A1 * | 2/2015 | Biedermann | A61B 17/7031 606/254 |
| 2015/0149126 | A1 * | 5/2015 | Maes | G06F 17/5086 703/1 |
| 2015/0297273 | A1 * | 10/2015 | Harris | A61B 17/8085 606/284 |
| 2016/0310184 | A1 * | 10/2016 | Kazanovicz | A61B 17/8061 |

FOREIGN PATENT DOCUMENTS

| | | |
|---|---|---|
| EP | 2474278 A2 | 7/2012 |
| RU | 2160067 C1 | 12/2000 |
| WO | 9921502 A1 | 5/1999 |
| WO | 0126566 A1 | 4/2001 |
| WO | 2004032726 A2 | 4/2004 |

* cited by examiner

PLATES WITH COUNTERSINKS

CROSS-REFERENCE TO RELATED APPLICATIONS

The present application claims the benefit of the filing date of U.S. Provisional Patent Application No. 61/982,640 filed Apr. 22, 2014, the disclosure of which is hereby incorporated herein by reference.

BACKGROUND OF THE INVENTION

The present invention is directed to an improved method of bone fixation, more particularly, to a bone fixation plate with preformed countersinks.

Resorbable bone plates are often utilized in areas of the body that do not bear heavy loads. For instance, resorbable bone plates are widely utilized in correcting deformities or treating trauma of the skull. Existing resorbable bone plates are typically either formed with screw holes or as solid plates with no holes. A solid plate offers significant resistance to torsional, compression, and tensional distortion greater than that of a plate formed with holes.

During a typical operation utilizing a resorbable plate, a surgeon accesses the bone to which the plate will be attached. The surgeon determines, intraoperatively, where to place the screws in the plate. When using a plate with preformed holes, the screws may be placed through any of the preformed holes. However, when a solid plate is used, the plate must be countersunk at each screw location before drilling and tapping a screw hole in the plate. Countersinking allows the bottom of the screw head to be fully seated into the bone plate when the screw is fully inserted, and without such a step, the screw head will sit proud with respect to the upper surface of the plate.

The additional steps required in utilizing a solid plate increase surgery time and effort on the part of the surgeon. In certain instances, this may outweigh the benefits of additional strength gained by utilizing such plates. Therefore, a need exists for an improved bone fixation plate and method of implanting a bone fixation plate that balances the need for increased strength, but also reduces the amount of surgical time to utilize such a plate.

BRIEF SUMMARY OF THE INVENTION

A bone plate according to one aspect of the present invention includes an elongated base member comprising a solid bottom surface and a top surface having a plurality of countersinks configured to receive a screw-head. A bone plate according to one aspect of the disclosure has a substantially rectangular shape with filleted edges. In accordance with certain embodiments, the bone plate may be pliable when heated. The bone plate may be resorbable and can be formed of a polymeric material.

In one embodiment, countersinks can be arranged on a top surface of a bone plate in at least one row and at least one column. A countersink can extend from a top surface of a bone plate toward a bottom surface of a bone plate without extending completely through. A countersink can have a hemispherical, rectangular, or frustoconical shape and allow a top surface of a screw head to be coplanar with a top surface of a bone plate when a screw is fully inserted into a plate. In those embodiments having a plurality of countersinks, some of the countersinks may be of a different shape than others. The countersinks can be equidistant from each other. Plates according to the present invention may be of any known shape/configuration. For instance, although only shown as rectangular in shape with countersinks arranged in rows/columns, it is envisioned to provide plates of any shape with any hole arrangement suitable for their use.

A method of implanting a bone plate according to one embodiment of the disclosure can include selecting a bone plate for implantation, heating a bone plate in a heater until a bone plate is pliable, manipulating a bone plate to resemble the contours of a bone, drilling and tapping one or more screw holes in one or more countersinks through a plate, and inserting a screw into a screw hole to secure a plate to a bone. In some embodiments, the bone plate may be heated in a hot water bath. A screw used with the bone plate may be self-tapping and tap the bone. In other embodiments, the drilling step can include tapping the bone. The bone plate may also be trimmed as part of the implanting process. The bone which the plate is attached to can be a craniofacial or midfacial bone.

DETAILED DESCRIPTION

Figure 1:
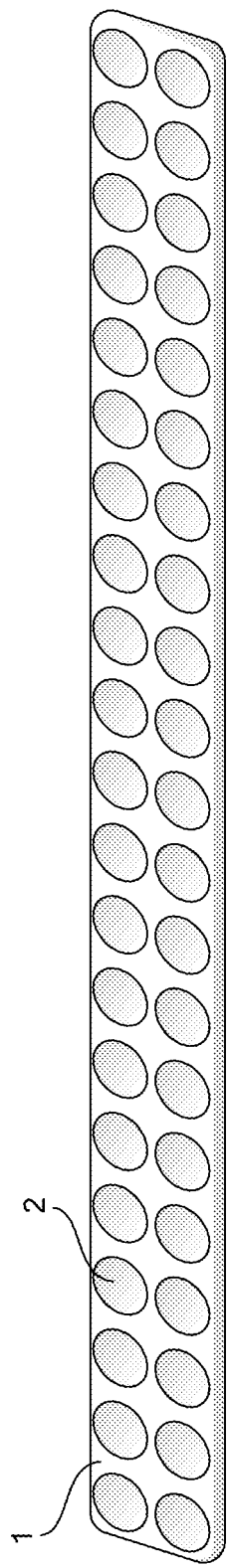
FIG. 1 is a perspective view showing an illustrative embodiment of a bone plate of the present invention.
Figure 2:
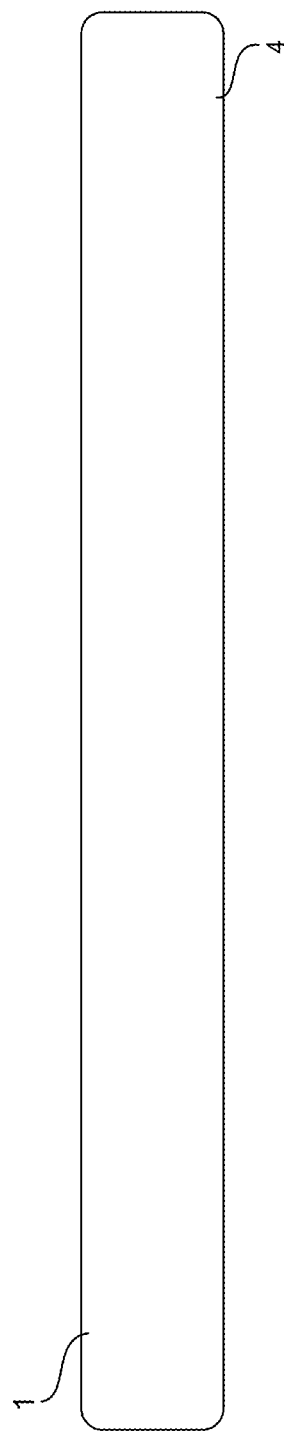
FIG. 2 is a bottom view of the bone plate of FIG. 1.
Figure 3:
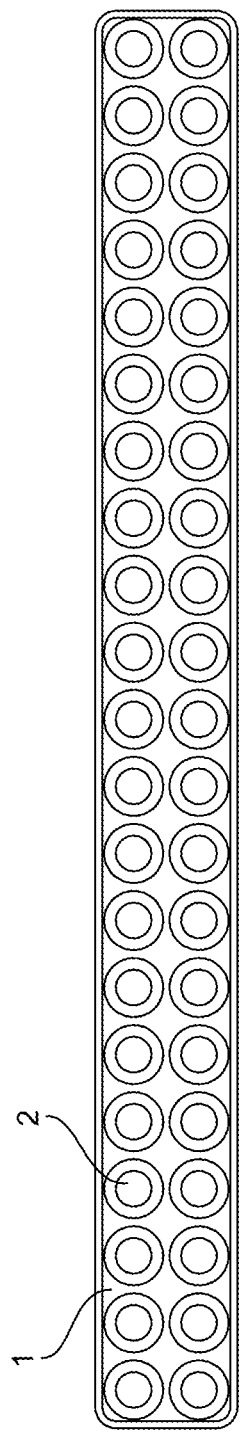
FIG. 3 is a top view of the bone plate of FIG. 1.

In a first embodiment, illustrated in FIGS. 1-5, a bone plate 1 includes a plurality of countersinks 2 formed on a top surface 3 of the bone plate 1. The plate 1, as shown in FIG. 2, has a solid bottom surface 4. The solid bottom surface, coupled with the other solid portions of plate 1, provides the plate with added strength and resistance to deformation than that of a similar plate with through holes formed through the plate in every portion where a countersink is shown.

In the embodiment shown in FIGS. 1-5, the plate 1 has an elongated, rectangular shape with rounded corners to minimize the risk of the implant causing irritation to a patient once implanted. Additionally, the perimeter of the top surface 3 of the plate 1 is filleted 5 to reduce any sharp edges formed on the plate. The countersinks 2 are shown in rows and columns equally spaced apart. The plurality of countersinks formed on the plate provides the surgeon with the option to choose the screw fixation points intaoperatively. In other words, instead of including a plurality of fully formed holes, the plate 1 includes the countersinks 2 that serve as preformed areas that can be utilized as fixation points.

Figure 4:
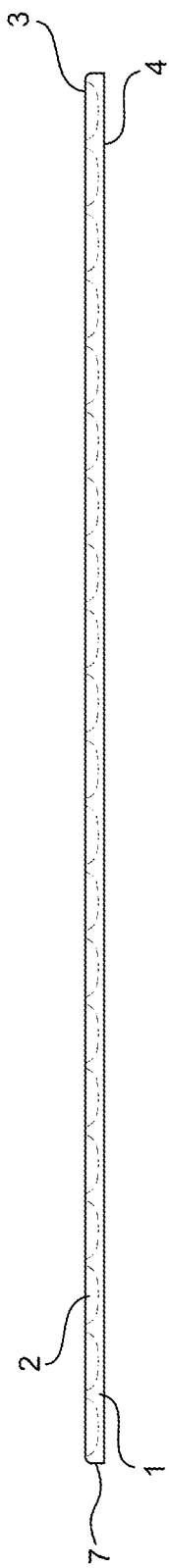
FIG. 4 is a side view of the bone plate of FIG. 1.
Figure 5:
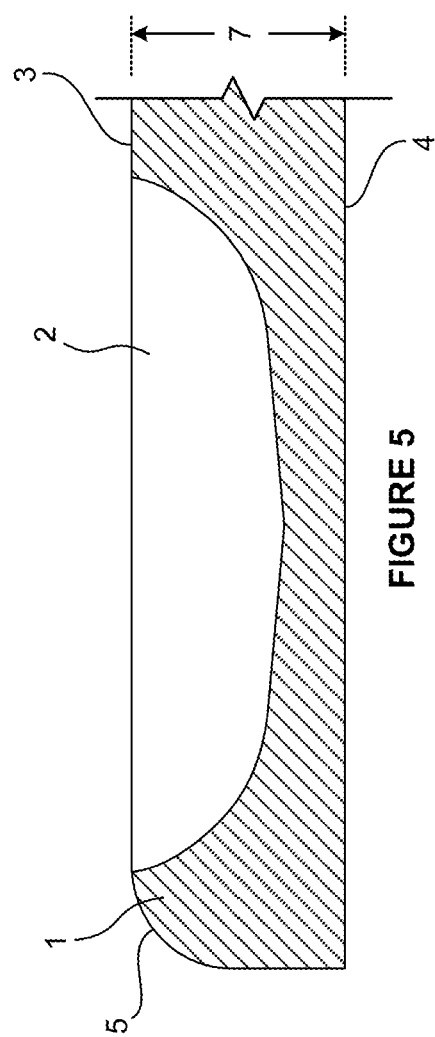
FIG. 5 is a cross-sectional view focusing on a single countersink of the bone plate of FIG. 1.

More particularly, as shown in FIGS. 4 and 5, the countersinks 2 extend from the top surface 3 toward the bottom surface 4 of the plate 1, but not entirely through the plate 1. A plate thickness 7 can be increased to improve overall strength of the plate, or decreased to reduce the volume of foreign material introduced into the body of a patient. In addition, it is contemplated to increase or decrease the overall size and/or depth of the countersinks 2 to increase the overall strength of the plate. The depth of each countersink could also be increased or decreased in selected regions of the bone plate to create regions of greater strength.

The countersinks 2 shown in FIG. 5 have a hemispherical shape to match the underside of a bone screw. However, other shapes are also contemplated such as a flat bottom, or other shape as necessary to match the underside of the bone screw used in cooperation with the plate. The diameter of the countersinks can be over-sized to enable the countersinks to receive a selection of screw heads, or have a diameter matching that of the specific screw heads to be used with the plate. The countersinks are not required to be of a singular shape. For example, some countersinks can be adapted to receive a screw head having a first shape while other countersinks are adapted to receive a screw head having a second shape.

The plate can be used in both adult and pediatric patients at any location where a bone needs to be fixed together and is preferably used in the craniofacial and midface skeleton. The plate can be manufactured to be resorbable by using a copolymer of polylactide and polyglycolide. The copolymer degrades and resorbs in vivo by hydrolysis into lactic and glycolic acid, which are then metabolized in the body to water ($H_2O$) and carbon dioxide ($CO_2$). A plate manufactured from the aforementioned copolymer is also malleable when sufficiently heated. The plate can be inserted into a heater, preferably a water bath, having a temperature of at least 140° F. for a maximum of 30 seconds. Once heated, the plate can be adjusted to match the contour of the bone to which the plate will be secured. The plate can also be trimmed after heating to adjust the length or width of the plate as desired thereby avoiding the implantation of unnecessary plate material into a patient. In a preferred embodiment, the plate is trimmed using surgical scissors.

Figure 6:
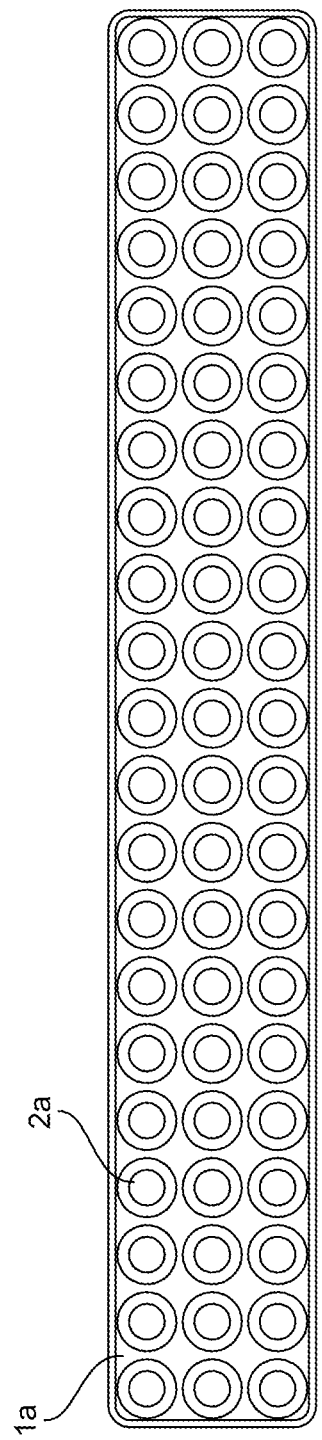
FIG. 6 is an alternative embodiment of the bone plate of FIG. 1.

FIG. 6 shows another embodiment of a bone plate 1a according to the current invention. In the embodiment shown, the plate 1a has three rows of countersinks. The plate 1a gives a surgeon more locations to choose from when choosing a position for a screw. The surgeon can also increase the total number of screws implanted to ensure complete fixation of the plate to the bone. Other configurations of the countersinks are also possible. For example, more rows or columns of countersinks could be included. The countersink pattern could also be something other than straight rows and columns. The space between the countersinks could also be increased, reducing the total number of countersinks formed on the top surface of the plate. Likewise, it is contemplated to provide plates of many different shapes and/or sizes for specific applications.

In use, the appropriately sized (e.g., length, width, thickness) and shaped bone plate 1 is first selected depending upon the bone or bones to be repaired. The selected plate is then placed into a heating apparatus, preferably a water bath, for up to 30 seconds. Once removed from the bath, the plate is malleable allowing it to be shaped to more closely match the contours of the bone to which it will be secured. After heating, the plate may also be trimmed to a desired length and/or shape by cutting with scissors or another cutting device. The surgeon can also trim the plate to a desired length after it has been attached to the bone.

Once the surgeon determines where to place the screws, screw holes can be drilled into the center of the selected countersinks and the bone can be tapped for the screw (preferably at the same time). Alternatively, the screws can be self-tapping, eliminating the need to tap the hole after drilling. After drilling the holes, the screw can be inserted until fully seated in the countersink and the bottom of the plate is secured against the bone.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A kit comprising:
    a bone plate comprising:
        a top surface;
        a bottom surface; and
        a plurality of countersinks formed in the top surface extending toward but not reaching the bottom surface;
        wherein the countersinks are each configured to receive a screw head, and
        wherein an arrangement of the countersinks is such that screws are selectively insertable in fewer than all of the countersinks to secure the bone plate to a bone, and
    a plurality of screws, wherein a total number of the plurality of screw is fewer than a total number of the plurality of countersinks.

2. The kit of claim 1, wherein the countersinks are arranged in at least one row and at least one column.

3. The kit of claim 1, wherein the bone plate is formed of a polymeric material.

4. The kit of claim 3, wherein the bone plate is pliable when heated.

5. The kit of claim 1, further comprising filleted edges.

6. The kit of claim 1, wherein at least one of the countersinks has a different depth than at least one other countersink to create an area with different bone plate strength characteristics.

7. The kit of claim 6, wherein at least one of the countersinks has a different shape than at least one other countersink to receive a different shaped screw head.

8. The kit of claim 1, wherein the countersinks are arranged in at least two rows and at least three columns.

9. The kit of claim 8, wherein the countersinks in each row and each column are equally spaced apart.

10. A method of implanting a kit including a plurality of screws and a bone plate having a plurality of countersinks formed in a top surface extending toward but not reaching a bottom surface of the bone plate, the method comprising:
    placing a bone plate against a bone;
    drilling a screw hole into the bone plate at a countersink;
    inserting a screw into the screw hole; and
    repeating the drilling and inserting steps at least once to secure the bone plate to the bone,
    wherein a total number of the plurality of screw is less than a total number of the plurality of countersinks.

11. The method of claim 10, further comprising heating the bone plate until pliable and manipulating the bone plate to match a contour of the bone.

12. The method of claim 11, wherein the step of heating the bone plate comprises placing the bone plate in a hot water bath.

13. The method of claim 10, wherein at least one of the plurality of screws is self tapping and taps the bone.

14. The method of claim 10, wherein the drilling step further includes tapping the bone.

15. The method of claim 10, further comprising trimming the bone plate.

16. The method of claim 15, wherein the trimming step occurs prior to securing the bone plate to the bone.

17. The method of claim 10, wherein the inserting a screw step comprises inserting a screw until a top surface of a screw head is aligned with the top surface of the bone plate.

18. The method of claim 10, wherein the bone is at least one of a craniofacial and midfacial bone.

19. A kit comprising:
a bone plate comprising:
an elongated base member having at least one filleted edge, wherein the elongated member is flexible when heated;
at least one row and at least one column of countersinks formed on an upper surface of the elongated member and extending toward a lower surface of the elongated member but not extending completely therethrough,
wherein the countersinks allow a top surface of a screw head to be co-planar with the upper surface of the elongated member when fully inserted, and
wherein an arrangement of the countersinks is such that screws are selectively insertable in fewer than all of the countersinks to secure the bone plate to a bone, and
a plurality of screws, wherein a total number of the plurality of screw is less than a total number of the plurality of countersinks.

20. The kit of claim 19, wherein the countersinks in each row and each column are equally spaced apart.

21. The kit of claim 19, wherein the countersinks have at least one of a hemispherical, rectangular, or frustoconical shape.

* * * * *